United States Patent [19]
Dysarz

[11] Patent Number: 5,129,884
[45] Date of Patent: Jul. 14, 1992

[54] TRAP IN BARREL ONE HANDED RETRACTED INTERVENOUS CATHETER DEVICE

[76] Inventor: Edward D. Dysarz, 11423 Triola Ln., Houston, Tex. 77072

[21] Appl. No.: 569,089

[22] Filed: Aug. 17, 1990

Related U.S. Application Data

[63] Continuation-in-part of Ser. No. 466,722, Jan. 16, 1990.

[51] Int. Cl.⁵ ............................................. A61M 5/178
[52] U.S. Cl. ..:............................. 604/164; 604/195
[58] Field of Search ............... 604/195, 263, 158, 159, 604/162, 163, 164, 198, 110, 187

[56] References Cited

U.S. PATENT DOCUMENTS

| | | | |
|---|---|---|---|
| 4,747,831 | 5/1988 | Kulli | 604/198 X |
| 4,813,940 | 3/1989 | Parry | 604/263 X |
| 4,834,718 | 5/1989 | McDonald | 604/163 X |

*Primary Examiner*—John D. Yasko

[57] ABSTRACT

An intervenous catheter device having a needle cannula fixed to a slidable piston. The slidable piston is held within the elongated hollow barrel of said intervenous catheter device by a compressed spring and a latch means. When said latch means is disengaged with said slidable piston fixed to said needle cannula, said slidable piston and said needle cannula are thrust into said elongated hollow barrel of said intervenous catheter device by said spring, said spring further holds said needle cannula fixed to said slidable piston within said elongated hollow barrel and is further prevented from being pushed out of said elongated hollow barrel by a rim in said elongated hollow barrel thus preventing any accidental injection of bacteria, virus or other undesirable material into others. The disengagement of said latch means with said slidable piston is accomplished with only one and the same hand that is used to inject the needle cannula into a body or into a vein inside of said body.

7 Claims, 3 Drawing Sheets

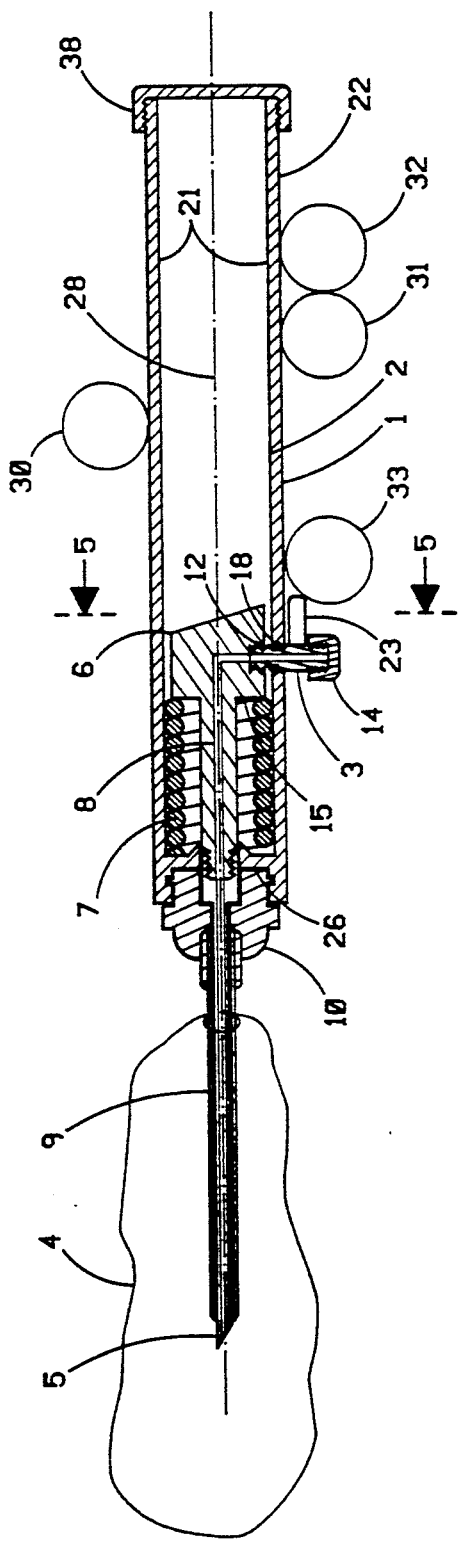
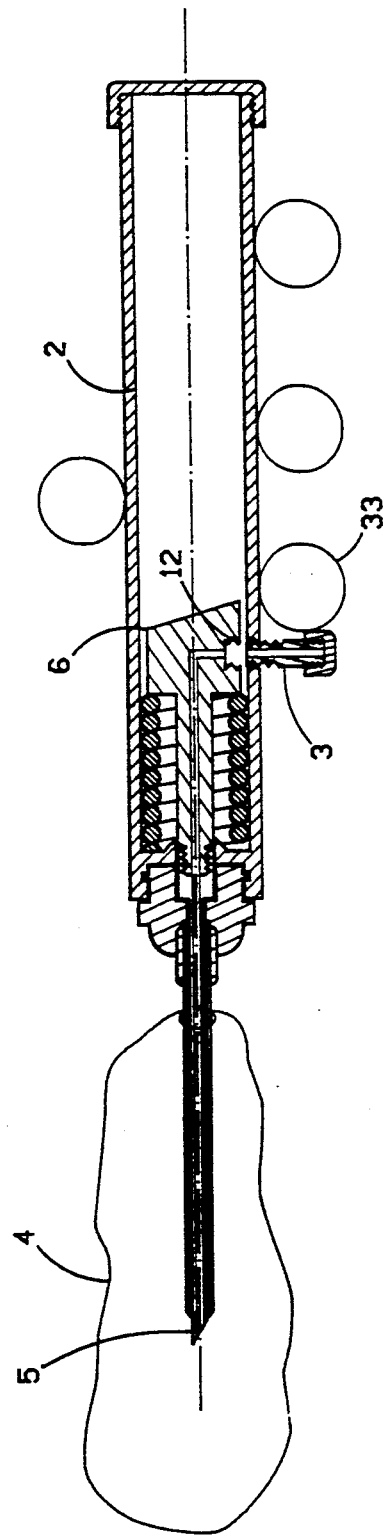

TRAP IN BARREL ONE HANDED RETRACTED INTERVENOUS CATHETER DEVICE

CROSS REFERENCE TO RELATED APPLICATIONS CONTINUATION

In part of U.S. patent application Ser. No. 07/466,722 filed Jan. 16, 1990, of Edward D. Dysarz which is incorporated and by reference. A one hundred retractable safety syringe.

BACKGROUND OF THE INVENTION

There are several types of safety intervenous catheter designs. Most of these designs are similar to syringes or blood sampling devices that are available today. One such design is shown in a patent issued to JAGGER et al on Jun. 3, 1986 U.S. Pat. No. 4,592,744. This is a safety blood sampling device however it requires two (2) hands to operate or to cover the needle cannula.

Blood samples are also taken with syringes and there are also many safety syringes available. Some of these designs have a sleeve or sheath that will cover the needle after it has been used. Some typical designs with sleeves or sheaths are Z. M. ROEHR et all U.S. Pat. No. 3,008,570, Z. M. ROEHR U.S. Pat. No. 3,107,785, BARTNER, et al U.S. Pat. No. 3,895,633, GK BURKE U.S. Pat. No. 3,306,291, GYURE et al U.S. Pat. No. 4,300,678, WINSTEAD HALL U.S. Pat. No. 4,356,822, SAMPSON U.S. Pat. No. 4,425,120, LARSON U.S. Pat. No. 4,639,249, HARBAUGH U.S. Pat. No. 4,655,751, STRAUSS U.S. Pat. No. 4,664,654, BRAGINETZ U.S. Pat. No. 466,435, SPENCER U.S. Pat. No. 4,702,738, MILORAD U.S. Pat. No. 4,702,739, SPENCER U.S. Pat. No. 4,801,295, PONCY U.S. Pat. No. 4,816,022, and HUGHES U.S. Pat. No. 4,840,619.

Other designs have a retractable needle such as WELTMAN U.S. Pat. No. 3,306,290, and DENT U.S. Pat. No. 4,392,859. These designs do not have a means whereby the needle is extended from the syringe and held in place in a positive and rigid position in order to first inject the needle prior to injecting the medication. Still other designs have methods of bending the needle to render it harmless after the medication has been injected. Most of these designs have one major purpose and that is to prevent the spread of infectious diseases such as aids, hepatitis, or other diseases from an accidental injection with a contaminated needle into others after the needle of the syringe was inserted into a patient with the above mentioned disease. These various designs all work well to a degree, but they all fall short of their intended purpose during the act of covering the needle, or removing the needle, which requires two hands.

All of these designs require at least two hands to operate. The use of two hands to cover the contaminated needle is most unsatisfactory in that during the act of placing a second hand on the intervenous catheter device or syringe, the person holding the intervenous catheter device or syringe in one hand may be bumped and accidentally inject the needle into their other hand before it can grasp the syringe. Other accidental jabbing or injections can happen in an ambulance where just as a person tries to grasp the contaminated intervenous catheter device or syringe, the ambulance can hit a bump in the road causing the person holding the intervenous catheter device or syringe to accidentally stick another person or themselves with the contaminated needle. The need has developed for an intervenous catheter device or syringe that will cover the contaminated needle with the use of only one hand.

SUMMARY

It is the object of this invention to provide an intervenous catheter device wherein the needle of the intervenous catheter device is retracted into the barrel of the intervenous catheter device and protects others from an accidental pricking after it has been used; the needle can be retracted into the barrel with the use of only one hand and that one hand being the hand that was used to inject the needle cannula into a patient.

Another object of the present invention is to render the needle cannula of the intervenous catheter device useless after the needle is retracted into the barrel of the intervenous catheter device to prevent the accidental reuse of the contaminated needle or to further prevent the reuse and abuse by users of illicit drugs.

It is still another object of the present invention to further prevent the accidental release of the needle cannula after the needle cannula is in the barrel of the intervenous catheter device.

The foregoing and other objects and advantages are attained by a device, an elongated hollow barrel, a needle cannula, spring, slidable piston, and barrel flange in combination with a latching means wherein when said intervenous catheter is used to inject a needle cannula into a vein in the body or part of the body in order to inject medication or other fluid at a consistent rate into the body, the latch means is released and the spring further pushes the needle cannula fixed to the slidable piston into the elongated hollow barrel of the intervenous catheter device rendering the contaminated needle harmless to prevent the accidental pricking of others and to prevent a contaminated needle from being released from the barrel of the intervenous catheter device.

The features of the present invention can be best understood together with further objects and advantages by reference to the following descriptions taken in connection with accompanying drawing, wherein like numerals indicate like parts.

BRIEF DESCRIPTION OF THE DRAWINGS

FIG. 1 is a section elevation view of the preferred embodiment of the present invention.

FIG. 2 is a section elevation view of the preferred embodiment showing the latch means being withdrawn from the slidable piston.

DETAILED DESCRIPTION OF THE PREFERRED EMBODIMENTS

Figure 3:
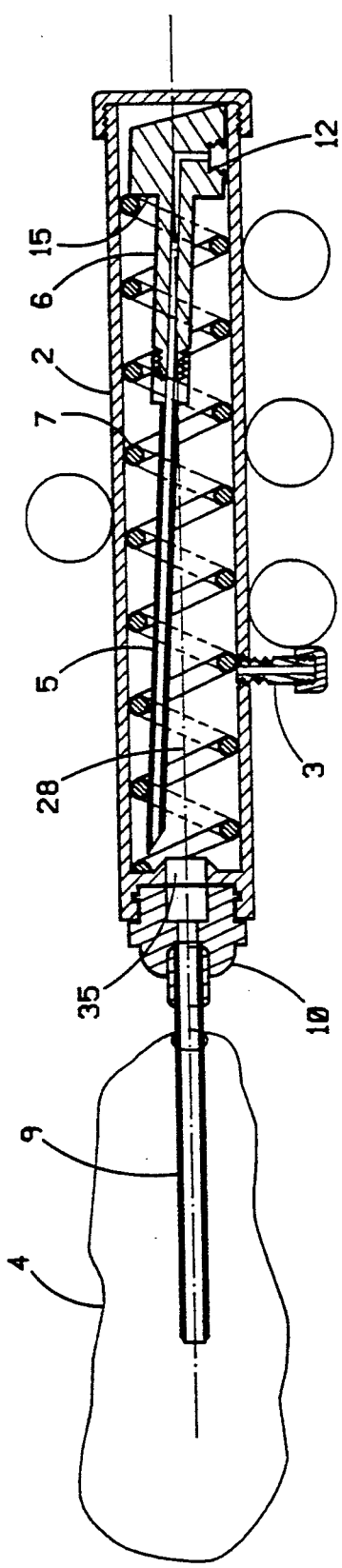
FIG. 3 is a section elevation view of the preferred embodiment of the intervenous catheter device showing the slidable piston assembly with the needle cannula pushed into the elongated hollow barrel by the spring.

Referring to FIG. 1 there is shown a section elevation view of the intervenous catheter device 1 of the preferred embodiment.

The intervenous catheter device 1 is comprised of an elongated hollow barrel 2 which is a round tube in configuration with a first end and a second end and with an inner surface 21 and an outer surface 22. The barrel flange 26 and the sort catheter fastener 10 is shown at the first end of the elongated hollow barrel 2; the cap 38 is shown at the second end of the elongated hollow barrel 2. The barrel flange 26 retains the spring 7 within the elongated hollow barrel 2. The elongated hollow barrel 2 has a longitudinal axis 28 in the center of the elongated hollow barrel 2. The longitudinal axis 28 has a first end at the first end of the elongated hollow barrel 2 and a second end at the cap 38 and runs the entire length of the elongated hollow barrel 2.

Also shown inside of the elongated hollow barrel 2 is the slidable piston 6 with a first end fixed to the second end of the needle cannula 5, the second end of the slidable piston 6 slopes and is not perpendicular to the longitudinal axis 28. The slidable piston 6 is shown held in place within the elongated hollow barrel 2 by the latch means 3 and the inner surface 21 of the elongated hollow barrel. The slidable piston 6 is further held in place at the first end by a compressed spring 7. The compressed spring 7 has a first end resting on the barrel flange 26 and a second end integral with the piston flange, 15. The compressed spring 7 is pushing on the piston flange 15 of the slidable piston 6. The slidable piston 6 is held and restrained in place by the latch means 3 on one side of the elongated hollow barrel 2. The latch means 3 is shown threaded into the piston notch 12 that is formed in the slidable piston 6. The latch 3 further extends from the slidable piston 6 and through the threaded latch hole 18 formed in the side of the elongated hollow barrel 2. The latch means 3 is threaded and is held by the threads formed in the threaded latch hole and threaded latch notch.

The slidable piston 6 is further shown with a tunnel 8 or cannula formed inside of the slidable piston 6 and extending from the needle cannula 5 and into the latch means 3. The tunnel 8 further extends through the latch means where it is shown with a latch cap 14 that may be removed in order to fasten a tube or other device to the latch means 3.

The intervenous catheter device 1 is shown held between fingers 31, 32, and 33, and the thumb 30 when the needle cannula 5 and the soft catheter 9 is injected into the body 4 or vein not shown. Finger 33 is shown near the finger tab 23. The blood flows through the needle cannula and into the tunnel 8 through the latch means 3 with the latch cap 14 removed or with some other device fastened to the latch means 3 to indicated that a vein or artery has been entered. The blood may flow under its own pressure, or it may have to be drawn out by some other means.

Referring to FIG. 2, there is shown the needle cannula 5 in the body 4 or vein or artery and the finger 33 has turned or rotated the latch bar to rotate the latch means 3 causing the latch means 3 to unscrew itself from the threaded piston notch 12, thus removing the latch means 3 from the piston notch that is restraining the slidable piston 6 within the elongated hollow barrel 2.

Referring to FIG. 3, there is shown a section elevation of the elongated hollow barrel 2 of the intervenous catheter device after the latch means 3 has been disengaged from the piston notch 12 of the slidable piston 6.

The spring 7 has thrust or pushes on the piston flange 15 causing the slidable piston 6 and the needle cannula 5 to move into the elongated hollow barrel 2 further causing the slope of the slidable piston 6 and the needle cannula 5 to slope within the elongated hollow barrel 2 relative to the longitudinal axis 28. This slope of the slidable piston 6 and the needle cannula 5 will prevent the needle cannula 5 from reentering the needle cannula tunnel 35 thus rendering the needle cannula 5 safe from the accidental pricking of a person. The constant pressure of the spring 7 will also prevent the needle cannula 5 from reentering the needle cannula tunnel 35. The soft catheter 9 is left in the body 4 or vein or artery. The soft catheter fitting 10 is left on the soft catheter 9 and is used to attach other tubes or devices that will allow fluid to flow into the body 4 or vein or artery.

Figure 4:
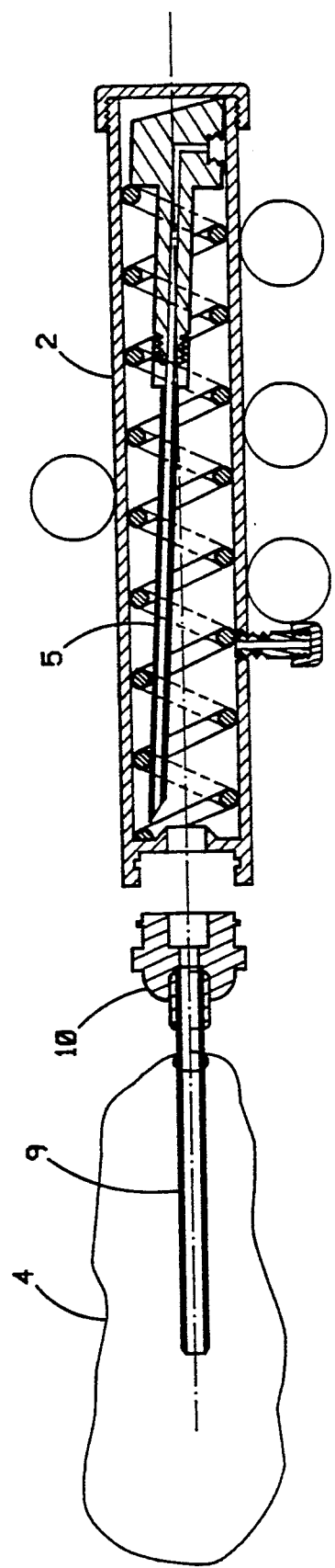
FIG. 4 is a section elevation view of the preferred embodiment showing the plastic soft catheter disengaged with the elongated hollow barrel.

Referring to FIG. 4, there is shown a section elevation of the intervenous catheter after it is disengaged with the elongated hollow barrel 2.

The intervenous catheter referred to as the soft catheter 9 is left in the body 4 or vein or artery. The soft catheter 9 is flexible and soft and will not damage the body 4 or vein or artery as a metal catheter would, however, a metal needle cannula 5 is required to break into or penetrate the skin of the body 4 or the wall of the vein or artery in order to guide the soft catheter into the body or vein or artery. Once the soft catheter 9 has penetrated the body 4 or vein or artery, the needle cannula 5 is withdrawn, leaving the soft catheter 9 in the body 4 vein or artery. The soft catheter fitting 10 is also left fixed to the soft catheter 9. A tube device or some other device is fixed to the catheter fitting in order to allow fluid to flow into the body 4 or vein or artery. The elongated hollow barrel 2 with the spring, the needle cannula, the slidable piston, and latch means are either thrown away, recycled, reused or disposed of in any suitable manner.

The elongated hollow barrel 2 is fixed to the soft catheter fitting by threads or other suitable means that will allow the elongated hollow barrel to be easily engaged and disengaged with the soft catheter fitting 10.

Figure 5:
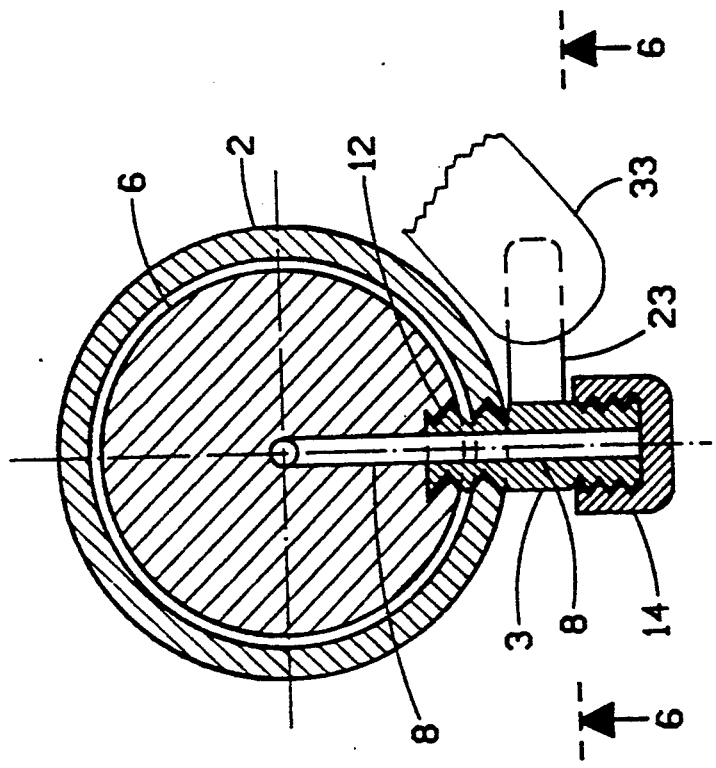
FIG. 5 is an enlarged section view of the latch means.

Referring to FIG. 5 there is shown a section elevation of the latch means 3 as taken through FIG 1.

The latch means 3 is shown going through the longitudinal hollow barrel 2 and into the threaded piston notch 12 of the slidable piston 6. The tunnel 8 or cannula is shown in the slidable piston 6. The tunnel 8 is also shown in the latch means 3 and it ends at the latch cap 14.

To remove the latch means 3 from the slidable piston 6, a finger 33 is pressed against the finger tab 23 causing the latch means 3 to rotate and further causing the latch means to unscrew out of the threaded piston notch 12 in the slidable piston 6.

Figure 6:
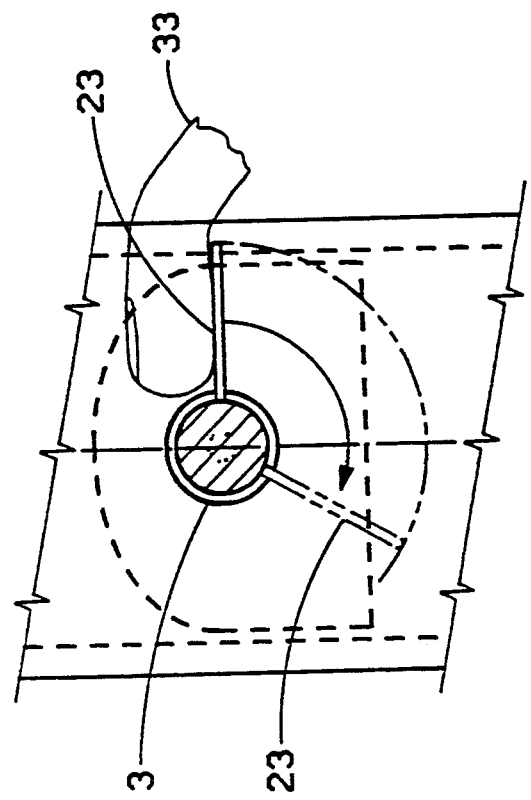
FIG. 6 is a section elevation of the latch means as taken through FIG. 5.

Referring to FIG. 6, there is shown a section view as taken through FIG. 5.

As the finger tab 23 is rotated by a finger 33, the latch means 2 is unscrewed from the slidable piston 6 thus releasing the slidable piston.

Although the system described in detail supra has been found to be most satisfactory and preferred many variations are possible. For example, the intervenous catheter device may have two or more latch means, the intervenous catheter device could be square in section or the latch means could be placed closer to the needle cannula.

Although the invention has been described with reference to the preferred embodiment, it will be understood by those skilled in the art, that additions, modifications, substitutions, deletions, and other changes not specifically described, may be made in the embodiments herein, it should be understood that the details herein are to be interpreted as illustrative and are not in a limiting sense.

I claim:

1. What is claimed as invention is:

an intervenous catheter device held by fingers and thumb for inserting a needle cannula and a catheter into a body and withdrawing said needle cannula from said body comprising:

an elongated hollow barrel having a first end and a second end and having an inner surface and an outer surface and further having a longitudinal axis in the center of the said elongated hollow barrel, parallel in most part of the said inner surface and said outer surface of the said elongated hollow barrel and further extending from said first end to said second end of said elongated hollow barrel;

a barrel flange fixed near to said first end of said elongated hollow barrel, said barrel flange further including a needle cannula tunnel formed in said barrel flange to allow said needle cannula to extend past said barrel flange;

a slidable piston inside of said elongated hollow barrel, said slidable piston having a first end and a second end and said first end of said slidable piston is nearer said first end of said elongated hollow barrel;

a soft catheter, said soft catheter having a first end and a second end, said second end is fixed to said first end of said elongated hollow barrel, said soft catheter further has a cannula extending from said first end of said soft catheter to said second end of said soft catheter;

a soft catheter fitting fixing said soft catheter to said elongated hollow barrel;

a needle cannula having a first end a second end, said first end of said needle cannula extends past said first end of said elongated hollow barrel and said second end of said needle cannula is fixed to said first end of said slidable piston, said needle cannula is disposed within said cannula of said soft catheter and said first end of said needle cannula extends past said first end of said soft catheter;

a spring means having a first end and a second end, said first end of said spring means is integral with said barrel flange of said elongated hollow barrel and said second end of said spring means is integral with said slidable piston, and spring means is further compressed between said barrel flange of said elongated hollow barrel and said slidable piston;

at least one piston notch formed into said slidable piston, said piston notch is near perpendicular to said longitudinal axis of said elongated hollow barrel;

a tunnel, said tunnel is formed inside of the said slidable piston, said tunnel is fixed to the needle cannula to allow fluid or blood to flow through the said needle cannula and into and through said tunnel formed in said slidable piston;

a needle cannula tunnel in said barrel flange;

at least one latch means for engaging and locking said slidable piston to said elongated hollow barrel and for disengaging said slidable piston and releasing said slidable piston from said elongated hollow barrel wherein said slidable piston is no longer restrained and said spring pushes said slidable piston and said needle cannula in the direction of the second end of said elongated hollow barrel until the said needle cannula is past the said barrel flange of the elongated hollow barrel, thus enclosing said needle cannula in said elongated hollow barrel and said barrel flange.

2. The intervenous catheter device of claim 1, wherein said slidable piston has a slope on the second end of said slidable piston.

3. The intervenous catheter device of claim 1, wherein said elongated hollow barrel has a cap on the second end, said cap to prevent said slidable piston and said needle cannula from being removed unintentionally.

4. The intervenous catheter device of claim 3, wherein when said slidable piston and said needle cannula are retracted into said elongated hollow barrel, and wherein said slope at said second end of said slidable piston will push against the said cap at said second end of said elongated hollow barrel further causing said slidable piston and said needle cannula to slope inside of said elongated hollow barrel.

5. The intervenous catheter device of claim 3, wherein said soft catheter will remain in said body or vein or artery after said needle cannula has been removed from said body or vein or artery 6. The intervenous catheter of claim 1 wherein said elongated hollow barrel may be disengaged with said soft catheter fitting.

7. The intervenous catheter device of claim 1 wherein said soft catheter and said soft catheter fitting may be attached to other suitable devices.

* * * * *